United States Patent [19]

Villax

[11] 4,061,676

[45] Dec. 6, 1977

[54] RECOVERY OF DOXYCYCLINE AND PRODUCTS THEREOF

[76] Inventor: Ivan Villax, 1, Travessa do Ferreiro, Lisbon-3, Portugal

[21] Appl. No.: 669,655

[22] Filed: Mar. 23, 1976

Related U.S. Application Data

[63] Continuation of Ser. No. 159,462, July 2, 1971, abandoned.

[30] Foreign Application Priority Data

| July 3, 1970 | Portugal | 54109 |
|---|---|---|
| Sept. 10, 1970 | Portugal | 54109 |
| June 9, 1971 | Portugal | 54109 |

[51] Int. Cl.² .......................................... C07C 103/19
[52] U.S. Cl. ............................................. 260/559 AT
[58] Field of Search ............................... 260/559 AT

[56] References Cited

U.S. PATENT DOCUMENTS

| 3,280,188 | 10/1966 | Villax | 260/559 AT |
|---|---|---|---|
| 3,397,231 | 8/1968 | Korst | 260/559 AT |
| 3,637,463 | 1/1972 | Villax | 260/559 AT |
| 3,795,707 | 3/1974 | Luciano | 260/559 AT |

FOREIGN PATENT DOCUMENTS

| 1,122,480 | 8/1968 | United Kingdom | 260/559 AT |
|---|---|---|---|

*Primary Examiner*—Donald G. Daus
*Assistant Examiner*—Mark L. Berch
*Attorney, Agent, or Firm*—Ostrolenk, Faber, Gerb & Soffen

[57] ABSTRACT

The present invention provides a process for the recovery of doxycycline and products thereof.

7 Claims, No Drawings

RECOVERY OF DOXYCYCLINE AND PRODUCTS THEREOF

This is a continuation of application Ser. No. 159,462, filed on July 2, 1971, now abandoned.

Various processes have been described for the preparation of α-6-deoxytetracyclines, also called 6-epi-6-deoxytetracyclines, of which the most important is the α-6-deoxy-5-hydroxytetracycline, commonly designated by the name of doxycycline, one of the most effective broad spectrum antibiotics.

U.S. Pat. No. 3,200,149 obtains the α-6-deoxytetracyclines by catalytic hydrogenation of 6-deoxy-6-demethyl-6-methylenetetracyclines or their 11a-chloro or fluoro derivatives.

U.S. Pat. Nos. 3,165,531, and 3,484,483 prepare them from the 13-benzylthio-α-6-deoxytetracyclines, the first one by reduction with Raney-nickel, and the second converts those same intermediates by reacting with a tri(lower alkyl) phosphite.

U.S. Pat. No. 3,849,491 obtains the α-6-deoxytetracyclines by reducing the 11a-halo-6-deoxy-6-demethyl-6-methylenetetracyclnes with hydrazine in the presence of a catalytic amount of carbon palladium or platinum, and finally, U.S. Pat. No. 3,849,491 submits the N,N'-dibenzylethylenediamine and N,N'-dibenzylethylenediimine molecular complexes of 11a-chloro-6-deoxy-6-demethyl-6-methylenetetracyclines, either to catalytic hydrogenation or to reduction with hydrazine, with a view to obtaining the respective new molecular complexes of α-6-deoxytetracyclines.

The reduction of the exocyclinc double bond at C6- gives a simultaneous raise of the two epimers α and β, the proportion of which depends on the reaction conditions. In U.S. Pat. Nos. 3,165,531 and 3,484,483, the 6-methyl group is already present in the α-6-position, consequently no β-isomer can be present.

However, the yields of all these known processes as far as α-isomer is concerned are much below 50%, the remaining representing besides the β-isomer, when present, a mixture of various secondary products, including apotetracyclines, 4-epi and mainly 5a-6-anhydro derivatives. The crude reaction product of any of the above processes is characterized by a high ultraviolet absorption at the 260-270 mμ region, the $E_{1cm}^{1=}$ being superior, often much superior, to 450 (value calculated on the doxycycline content), whereas pure doxycycline exhibits an $E_{1cm}^{1=}$ of 410 at 266 mμ.

The isolation and purification of α-6-deoxytetracyclines from the crude reaction mixture was until now a complicated procedure, giving low yields and difficult to perform in an industrial scale.

In prior art (U.S. Pat. No. 3,200,149), chromatographic separation and counter-current distribution were applied as purification processes, or larger amounts of the α-6-deoxytetracyclines have been obtained by conventional methods in tetracycline chemistry, such as precipitation of the active product from the reaction mixture as an insoluble acid addition salt, usually as 5-sulfosalicylates. However, the crude sulfosalicylate, thus obtained, was extremely impure: $E_{1\,cm}^{1\%}$ 110-150 at 349 mμ and $E_{1\,cm}^{1\%}$ 340-500 at 268 mμ, specific rotation: $/a/_D$ −150 to −200, as compared with $E_{1\,cm}^{1\%}$ cm 220-225 at 349 mμ and $E_{1\,cm}^{1\%}$ 270-285 at 268 mμ, specific rotation: $/a/_D$ −85 to −90, when the 5-sulfosalicylate of doxycycline is produced according to the present invention.

The sold industrially useful process which exists in previous art for the purification of this crude sulfosalicylate is described in French Pat. No. 1,570,644, which consists of two steps, i.e., recrystallization of the sulfosalicylate from hot absolute methanol containing anhydrous hydrogen chloride, followed by transformation of the sulfosalicylate, thus recrystallized, into hydrochloride by dissolving it in hot absolute ethanol containing hydrogen chloride, then provoking transformation of the sulfosalicylate into hydrochloride hemiethanolate hemihydrate by the addition of concentrated aqueous hydrochloric acid or water in a proportion of not less than 3% and not more than 11%. The product, thus obtained, according to our experience, although it contains only 5 to 8% impurities, is of a dark-yellow colour with dark-brown speckles.

The present invention refers to a simple process which permits one to isolate the α-6-deoxytetracyclines directly from the reaction mixture, obtained according to any of the above mentioned processes, with a high purity, either as an insoluble acid addition salt or as a molecular complex.

Furthermore, this invention is based on the observation according to which the major part of the by-products present in the crude reaction mixtures are easily destroyed by an aqueous acid at a temperature comprised between 60° and 90° C, within a period of 15 to 90 minutes, without destruction of any appreciable amount of the desired α-6-deoxytetracyclines in such a way that the destruction product does not interfere with the subsequent selective precipitation of the α-6-deoxytetracyclines. According to the present invention, this acid treatment is followed by selective precipitation of the α-6-deoxytetracyclines from the reaction mixture, either as an acid addition salt or as the N,N'-dibenzylethylenediamine or N,N'-dibenzylethylenediimine molecular complex, with a high degree of purity.

Thus, the present process represents a considerable simplification over that described in French Pat. No. 1,570,644 by obtaining, directly from the reaction mixture, a practically pure acid addition salt or a molecular complex which need not to be recrystallized before converting into a base or into a pharmaceutically useful acid addition salt. Furthermore, it avoids the use of the expensive anhydrous methanol and ethanol or a methanolic solution of anhydrous hydrogen chloride, and all the inherent inconveniences of their manipulation.

Another feature of the present invention is that it prepares the base of the α-6-deoxytetracyclines as the monohydrate directly from the acid addition salts, thus obtained, with a nearly stoichiometric yield (over 90%), by neutralizing the acid addition salt with a tertiary amine in aqueous ethanol. In the prior art, such a transformation gives yields of 63%, thus the present invention provides a process and specific conditions thereof to obtain not only industrially useful yields through a "per se" conventional method, but the transformation which is carried out under the reaction conditions as specified is also accompanied by a simultaneous further purification.

When the active product is precipitated with the aid of N,N'-dibenzylethylenediamine (DBED) or N,N'-dibenzylethylenediimine (Δ-DBED) in the presence or absence of earth-alkali metal ions, at a pH between 3.5-7.5, from the complexes thus obtained, the hydrochloride can be liberated directly by treating them with hydrochloric acid in ethanol. In any other acid addition salt is desired, one acidifies the complexes by the desired acid in a medium where the preferred acid addition salt of the α-6-deoxytetracyclines is little soluble and the respective DBED acid addition salt is soluble. In the case of Δ-DBED complexes, the N,N'-dibenzylethylenediimine decomposes itself in the strongly acid medium.

Finally, this invention also provides a process to prepare the hitherto not characterized calcium salt of the α-6-deoxytetracyclines, which is particularly useful for the preparation of oral suspensions.

All of the above mentioned processes for the preparation of a α-6-deoxytetracyclnes utilize organic media miscible with water to perform the reduction. The present invention is applicable to a reaction medium containing any organic solvent, however, those containing a water miscible medium are the preferred ones. The acid treatment can be performed with any organic or inorganic acid, strong enough to cause destruction of the by-products present and which will not attack otherwise the α-6-deoxytetracyclines molecules or cause epimerization at C4-. Such unsuitable acids are for instance nitric acid and acetic acid. Satisfactory results may be obtained by using diluted sulphuric acid, however, the preferred acid is hydrochloric acid which will not interfere with the subsequent formation of the acid addition salt nor with that of the molecular complexes. The final concentration of hydrochloric acid in the reaction mixture is from 2 to 18%. A higher concentration can be used, however, no additional benefit is obtained. Destruction of the by-products occurs preferably between 60° to 90° C. Below this limit, the destruction is slow, and above the α-6-deoxytetracyclines are partially destroyed. The preferred temperature range is between 68° to 75° C. The time of heating necessary to effect destruction of the by-products is 15 to 90 minutes, that depending on the concentration of acid and the amount of by-products present. Usually 30 to 40 minutes at 70° C are sufficient to obtain the desired destruction of the by-products.

The reaction mixture is then cooled and the α-6-deoxytetracyclines are either precipitated directly as insoluble addition salts by addition of 5-sulfosalicylic acid forming the known sulfosalicylate. In order to obtain satisfactory yields, the reaction mixture should be sufficiently diluted with water to provoke a complete precipitation. The amount of water depends on the concentration of α-6-deoxytetracyclines and on the nature of the water miscible solvent present in the reaction mixture. A proportion of 1 part of organic solvent to 3 parts of water is usually sufficient to obtain a satisfactory precipitation.

When precipitating the α-6-deoxytetracyclines as molecular complexes, DBED or Δ-DBED is added in a stoichiometric excess to the acid treated and then diluted cool reaction mixture and the pH is adjusted between 3.5 and 5.0 with ammonia or diluted sodium hydroxide in order to obtain the respective DBED or Δ-DBED complexes. When using calcium, magnesium or strontium hydroxide, instead of ammonia or sodium hydroxide, the respective metalo-N,N'-dibenzylethylenediamine or metalo-N,N'-dibenzylethylenediimine complexes are formed, the preferred pH range for complete precipitation being comprised between 5 and 7.5.

The acid addition salts or molecular complexes, thus precipitated, are subsequently filtered, washed with water, acetone or alcohol, and dried.

From the DBED or Δ-DBED complexes, thus obtained, one can obtain the α-6-deoxytetracyclines as acid addition salts by treating them with an acid in an organic solvent, eventually containing a small amount of water (0.5 to 5%). The hydrochloride hemiethanolate hemihydrate can be obtained directly by suspending the complexes in 95% alcohol and adding 5 to 10% concentrated hydrochloric acid. Instead of hydrochloric acid, any other acid can be used, i.e., methanesulfonic, p-toluenesulfonic, salicyclic, sulfosalicylic, ascorbic, acetic and lactic acid. The organic medium is preferably chosen in such a way that the acid addition salt formed should be little soluble in it.

Naturally, the α-6-deoxytetracyclines may already be present in the reaction mixture as DBED or Δ-DBED complexes. In this case, the acid destruction is performed in the same manner and in order to precipitate the complexes, an additional amount of DBED or Δ-DBED should be added.

From the acid addition salts of α-6-deoxytetracyclines, the free base can naturally be obtained by neutralizing the acid with a tertiary amine, as known in the art. According to the present invention, if the medium is ethanol containing 10 to 50% of water (2 to 4 times the volume per weight of the acid addition salt), the tertiary amine is added in a strictly stoichiometric account, and furthermore if, once the crystallization has started, an additional amount (1 to 2 times the whole volume) of ethanol is added to the reaction mixture, the transformation into the free base is nearly stoichiometrical and is accompanied by a substantial purification. The amphoteric product, thus obtained, does not contain concomitant traces of the acid addition salt. The preferred amine used for recrystallization is triethylamine, however, dimethylaminoethanol, diethylaminoethanol or triethanolamine also gives satisfactory results.

The calcium salts of the tetracyclines are known to be particularly suitable for the preparation of stable oral suspensions. However, the preparation of the calcium salt of doxycycline represents considerable difficulties due to the great instability of the molecule at an alkaline pH range. Consequently, when trying to prepare the calcium salt of doxycycline, according to known processes, a considerable loss of yield and activity occurred and the dried product was of greenish tinge. According to the present invention, a stable and easy filterable calcium salt of doxycycline can be prepared by suspending doxycycline hydrochloride in 80% aqueous methanol, adjusting the pH from 5.5 to 6.2 and subsequently adding half a mole of a high purity calcium hydroxide per each mole of doxycycline.

The process described in accordance with the present invention is applicable to the isolation, in pure state, of all known α-6-deoxytetracyclines, the most important of which are α-6-deoxytetracycline, α-6-deoxy-7-chlorotetracycline and α-6-deoxy-5-hydroxytetracycline.

The examples hereunder are given by way of illustration and are not intended to limit the scope of the claims of the present invention.

EXAMPLES 12500 grs. of amphoteric 11a-chloro-6-deoxy-6-demethyl-6-methylene-5-hydroxytetracycline is hydrogenated in 27500 mls. of dimethylformamide in the presence of 5% palladium carbon at a pressure of 4 kg/cm² and the formed hydrogen chloride is continuously neutralized by adding triethylamine in dimethylformamide to the reaction mixture, maintaining a constant pH.

After hydrogenation, it is filtered, mixed with 1500 grs. of terra-silica, and the cake is washed with 31 lts. of aqueous dimethylformamide 50%. In accordance with the present invention, to the filtrate thus obtained 27.5 lts. of concentrated hydrochloric acid is added. The reaction mixture thus acidified is heated up to 68° C and maintained at a temperature range of 68° to 72° C during 30 minutes. It is then cooled quickly to 50° C and 12000 grs. of 5-sulfosalicyclic acid and 35 lts. of water are added. After stirring during 2 hours at 15° C, the crystalline precipitate is collected by filtration, washed with aqueous methanol 60%, then with acetone and ether. The dry product weighs 8360 grs. Melting point 206°–212° C with decomposition; $E_{1\,cm}^{1\%}$ 286 at 268 m$\mu$ and 221 at 349 m$\mu$ (in methanol containing 1% hydrochloric acid; specific rotation $/\alpha/_D -85$ ($c=0.5$ in 1% hydrochloric acid in methanol). The thin layer chromatography (on infusorial earth plated out with a 5% aqueous solution of edetic acid containing 5% glycerin-impregnating solution: McIlvain buffer (pH 3.7) containing 5% glycerin; mobile phase: ethyl acetate saturated with the impregnating solution) presents a slight non-mobile spot, an extremely slight halo at the $R_f$ corresponding to the $\beta$-isomer and a strong spot of doxycycline sulfosalicylate at $R_f$ 0.46.

2. 8360 grs. of the sulfosalicylate obtained in Example 1 is suspended in a mixture of 15 lts. of ethanol and 4 lts. of water, and 3260 mls. of triethylamine in 3260 mls. of ethanol is then added. It is stirred, and when crystallization becomes so thick that stirring becomes difficult, 30 lts. of ethanol is added. After stirring for an additional hour, the product is filtered, washed with 21 lts. of ethanol, 10 lts of acetone and 8 lts. of ether. It is dried at 40° C, yielding 4900 grs. of pure crystalline amphoteric doxycycline monohydrate. Melting point 174°–177° C with decomposition; $E_{1\,cm}^{1\%}$ 420 at 268 m$\mu$ and 330 at 349 m$\mu$ in methanol containing 1% hydrochloric acid. The pH of a 1% suspension in water is 5.5. Specific rotation $/\alpha/_D -110$ ($c=1$ in methanol containing 1% hydrochloric acid). Further amounts may be recovered from the collected mother-liquors by diluting with water and adding sulfosalicyclic acid, which permits to attain an overall yield of 95%, expressed in total recovered doxycycline.

3. 4525 grs. of the doxycycline base obtained in Example 2 is dissolved in a mixture of 4525 mls. of ethanol, 2260 mls. of water and 980 mls. of concentrated hydrochloric acid. After stirring during 15 minutes, 9000 mls. of ethanol containing 17.5% of hydrogen chloride plus 2260 mls. of concentrated hydrochloric acid is added, and after stirring during 3 hours, the crystals thus formed are filtered, and the cake is washed with 5.5 lts. of ethanol. 2.8 lts. of ethyl acetate, 2.8 lts. of acetone, and finally with 2.8 lts. of ether. Yield: 4820 grs. of doxycycline hydrochloride hemiethanolate hemihydrate (hyclate). Melting point 209°–214° C with decomposition; specific rotation $/\alpha/_D -105$ ($c=1$ in methanol containing 1% concentrated hydrochloric acid); $E_{1\,cm}^{1\%}$ 381 at 268 m$\mu$ and 296 at 349 m$\mu$. A further amount of doxycycline may be recovered from the mother-liquors by diluting in 1 by 3 parts of water and adding 250 grs. of sulfosalicyclic acid. The total recovery yield is 98%.

4. The procedure of Example 1 is followed, but 6000 grs. of DBED-diacetate and 350 lts. of water are added to the acid treated and cooled reaction mixture, and the pH is adjusted with 10% sodium hydroxide to pH 3.4. The impurities thus precipitated are separated by filtration and calcium hydroxide is subsequently added until the pH reaches 6.5. After stirring during 30 minutes, the precipitate is filtered, washed with water and dried under a dry air stream at 40° C. The new DBED-calcium molecular complex of $\alpha$-6-deoxy-5-hydroxytetracycline, thus obtained, in the proportion of 1 mole of DBED, 1 atom of calcium and 2 moles of doxycycline, is insoluble in water and decomposes at 230° C. Specific rotation $/\alpha/_D -100$ ($c=1$ in methanol containing 1% concentrated hydrochloric acid); $E_{1\,cm}^{1\%}$ 313 at 253 m$\mu$ and 200 at 347 m$\mu$ in N/100 methanolic HCl. The principal peaks of the infrared curve in petroleum oil mull are at 2.98$\mu$, 6.23$\mu$, 6.7$\mu$, 8.05$\mu$, 8.2$\mu$, 8.65$\mu$, 8.92$\mu$, 9.65$\mu$, 10.05$\mu$, 10.7$\mu$, 12.04$\mu$, 12.3$\mu$. It is as active "in vitro" as its doxycycline content. The equivalent DBED doxycycline complex, in the proportion of 1 mole of DBED and 2 moles of doxycycline, containing no metal ion, has the following characteristics: It is insoluble in water and decomposes at 194° C; specific rotation $/\alpha/_D -110$ ($c=0.5$ in methanol containing 1% hydrochloric acid); $E_{1\,cm}^{1\%}$ 349 at 266–268 m$\mu$ and 267 at 348–352 m$\mu$ in methanol containing 1% hydrochloric acid. The infrared curve is comparable to that of the calcium containing complex, with the difference that the 6.7$\mu$ maximum is at 6.65$\mu$ and the maximum at 8.2$\mu$ is much more pronounced.

5. The procedure of Example 3 is followed, using 4500 grs. of the DBED-calcium doxycycline complex obtained in Example 4, instead of 8360 grs. of sulfosalicylate, and using 12 lts. of ethanol for washing the filtercake. Yield: 2600 grs. of doxycycline hyclate, the characteristics of which are comparable to those of the product obtained in Example 3.

6. Example 4 is repeated, but using 4000 grs. of $\Delta$-DBED instead of 6000 grs. of DBED-diacetate. The isolated product is the new $\Delta$-DBED-calcium doxycycline complex in the proportion of 1 mole of $\Delta$-DBED, 1 atom of calcium and 2 moles of doxycycline. $E_{1\,cm}^{1\%}$ 214 at 359 m$\mu$. The product, thus obtained, contains approximately 10% of impurities but still it may be converted into doxycycline hyclate, by applying the process as described in Example 5.

7. The crude sulfosalicylate of doxycycline obtained through the recovery process of Example 2 is reconverted into base as per the process described in said example. A 100 grs. portion thereof is subsequently dissolved in 300 mls. of water containing 40 mls. of concentrated hydrochloric acid. It is then treated with charcoal, stirred during 25 minutes and filtered from the insolubles. 300 mls. of ethanol containing 17% of hydrogen chloride is then added to the filtrate. The crystals formed are filtered after stirring during 3 hours, then washed with ethanol, acetone and ethyl ether, yielding doxycycline hyclate comparable in quality to that described in Example 3.

8. The reaction mixture, containing predominantly the $\alpha$-isomer, as obtained in U.S. Pat. No. 3,849,491 after it has been treated according to the processes described in Example 1, 2 and 3, yields the hydrochloride which consists of 41% of methacycline, 53% of doxycycline and 4% of $\beta$-isomer. 2000 grs. of this mixture is then dissolved in 6 lts. of water containing 100 mls. of concentrated hydrochloric acid. After stirring during 1 hours, it is filtered and washed with 1 lt. of 10% hydrochloric acid, and then with ethanol, acetone and ether. The insolubles consist of pure methacycline hydrochloride, its analytical values being comparable to those reported in the literature. 7 lts. of ethanol containing 17% of hydrogen chloride is then added to the filtrate thus obtained, after which the doxycycline hyclate crystallizes. After stirring during 4 hours, it is filtered and the cake is washed with ethanol, acetone and ethyl ether. The doxycycline hyclate, thus obtained, is comparable in quality to that obtained in Example 3; however, it does contain the β-isomer in a proportion of 3.6%.

9. When applying the process outlined in Examples 1, 2 and 7 to the final reaction mixture obtained according to the invention described in U.S. Pat. Nos. 3,200,149 and 3,484,483, a good quality α-6-deoxy-5-hydroxytetracycline is obtained.

What is claimed is:

1. A process for the recovery of α-6-deoxy-5-hydroxytetracycline in high purity from the crude reaction mixture resulting from the conversion of an intermediate into said α-6-deoxy-5-hydroxytetracycline and having the same as well as reaction by-products, degradation products and the β-isomer as impurities, said crude reaction mixture being the initial reaction mixture in which the α-6-deoxy-5-hydroxytetracycline is present prior to the institution of any recovery procedures, which consists essentially of the steps of (1) first acidifying said crude reaction mixture with a concentrated aqueous solution of methanesulfonic acid, sulphuric acid or hydrochloric acid, (2) then heating to a temperature of 60° to 90° C until said impurities are further degraded, (3) cooling said reaction mixture and then (4) precipitating said α-6-deoxy-5-hydroxytetracycline from said reaction mixture thus treated and cooled, in the form of water insoluble acid addition salts and molecular complexes selected from the group consisting of 5-sulfosalicylate, N,N'-dibenzylethylenediamine- and N,N'-dibenzylethylenediimine molecular complexes, N,N'-dibenzylethylenediamine alkaline earth metal and, N,N'dibenzylethylenediimine alkaline earth metal molecular complexes by adding the corresponding acid or molecular complex to said treated and cooled reaction mixture, said steps (1) – (4) being carried out sequentially without any intervening steps.

2. A process according to claim 1, wherein said reaction mixture containing the α-6-deoxy-5-hydroxytetracycline contains a water miscible solvent.

3. A process according to claim 1 wherein the final concentration of acid is between 2 to 18%.

4. A process according to claim 1 wherein the time for carrying out the acid treatment at 60° to 90° C is 15 to 90 minutes.

5. A process according to claim 1 wherein said acid addition salt is mixed with 2–3 times its volume per weight of aqueous ethanol containing 10 to 50% of water, neutralized with an equimolecular amount of a tertiary amine and diluted subsequently with an additional amount of ethanol to form said α-6-deoxy-5-hydroxytetracycline.

6. A process according to claim 1 wherein said α-6-deoxy-5-hydroxytetracycline is precipitated in the form of the N,N'-dibenzylethylenediamine calcium complex.

7. A process according to claim 6 wherein said complex is treated with ethanolic hydrochloric acid to form the hydrochloride.

* * * * *